United States Patent [19]

Akiyama

[11] 4,069,825
[45] Jan. 24, 1978

[54] SURGICAL THREAD AND CUTTING APPARATUS FOR THE SAME

[76] Inventor: Taichiro Akiyama, 19-23 Shimoochai 2-chome, Shinjuku, Tokyo, Japan

[21] Appl. No.: 653,243

[22] Filed: Jan. 28, 1976

[51] Int. Cl.² .............................................. A61L 17/00
[52] U.S. Cl. .................................................. 128/335.5
[58] Field of Search ................ 24/206 A; 128/303 R, 128/334 R, 335.5

[56] References Cited

U.S. PATENT DOCUMENTS

| 3,072,986 | 1/1963 | Lefnaer | 24/206 A X |
| 3,194,239 | 7/1965 | Sullivan | 128/335.5 |
| 3,463,436 | 8/1969 | Foster, Jr. | 24/206 A X |
| 3,762,418 | 10/1973 | Wasson | 128/335.5 |
| 3,918,455 | 11/1975 | Coplan | 128/335.5 |

FOREIGN PATENT DOCUMENTS

386,161   1/1933   United Kingdom ............. 128/335.5

Primary Examiner—Channing L. Pace
Attorney, Agent, or Firm—McDougall, Hersh & Scott

[57] ABSTRACT

A surgical thread includes a thread-like body and a plurality of projections formed at regular intervals in the thread-like body. A blood vessel can be simply and surely ligated with the surgical thread. A cutting apparatus for the surgical thread includes a holder for a surgical thread through which the surgical thread is inserted, a cutting member arranged adjacent to the holder, an actuating rod for actuating the cutting member, and a trigger for driving the actuating rod. Even when the blood vessel is ligated with the surgical thread in the interior of the human body, the surgical thread can be easily cut by the cutting apparatus in the interior of the human body.

9 Claims, 27 Drawing Figures

SURGICAL THREAD AND CUTTING APPARATUS FOR THE SAME

BACKGROUND OF THE INVENTION

1. Field of the Invention

This invention relates to a surgical thread and a cutting apparatus for the same, and more particularly to a surgical thread most suitably used as a ligature or a sewing or stitching thread.

2. Description of Prior Art

Hitherto, a thread or a filament of synthetic resin is widely used as a surgical thread such as a ligature or a sewing or stitching thread. The friction of the surface of such a conventional thread is little. Accordingly, for example, when the blood vessel is ligated with the conventional thread, the knotted thread is apt to loosen. The ligating condition is very unstable. In order to obtain the stable ligating condition, a double knot or a complicated knot of the conventional thread should be made. That is very troublesome. Even in the double knot, the conventional thread has the disadvantage that the thread ligating the blood vessel is apt to slide in the lengthwise direction of the blood vessel.

SUMMARY OF THE INVENTION

Accordingly, it is an object of this invention to provide a surgical thread which can overcome the above-described disadvantages of the conventional thread.

Another object of this invention is to provide a surgical thread by which the ligating operation of the blood vessel or the stitching operation of the incised tissue can be surely and simply effected.

A further object of this invention is to provide a surgical thread by which the blood vessel positioned inside the incised human body can be surely and simply ligated without drawing out the blood vessel from the inside of the incised human body.

A still further object of this invention is to provide a cutting apparatus by which the above-described surgical thread can be simply cut, even when the blood vessel positioned inside the incised human body is ligated with the surgical thread without drawing out the blood vessel from the inside of the incised human body.

In accordance with an aspect of this invention, a surgical thread includes a thread-like body and a plurality of projections formed at intervals in the thread-like body.

In accordance with another aspect of this invention, a cutting apparatus for the surgical thread includes a holder for a surgical thread through which the surgical thread is inserted, a cutting member arranged adjacent to the holder, an actuating rod for actuating the cutting member, and a trigger for driving the actuating rod.

The above and other objects, features and advantages of this invention will become apparent from the following detailed description of illustrative embodiments shown in the accompanying drawings.

DESCRIPTION OF THE PREFERRED EMBODIMENTS

A ligature for stopping bleeding, according to one embodiment of this invention will be described with reference to FIG. 1 to FIG. 8.

Figure 1:
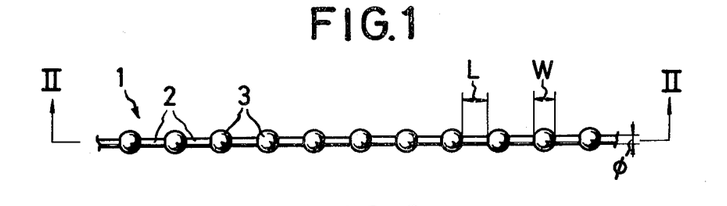
FIG. 1 is a plan view of a ligature according to one embodiment of this invention.
Figure 2:
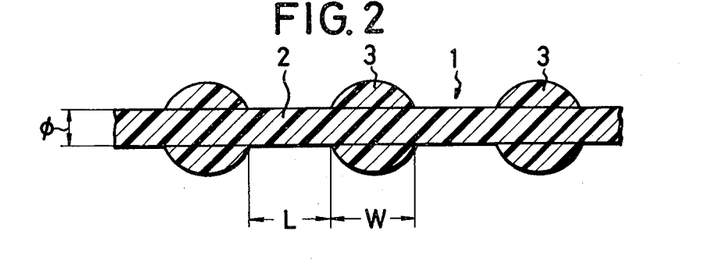
FIG. 2 is an enlarged cross sectional view of a part of the ligature, taken along the line II—II of FIG. 1.

Referring to FIG. 1 and FIG. 2, a ligature 1 comprises a thread 2 and spherical projections 3 which are formed integrally with the thread 2 at regular intervals. The thread 2 is formed of synthetic resin such as polyvinyl-alcohol. The diameter $\phi$ of the round cross-section of the thread 2 is 0.3 - 0.5 mm. For example, it is 0.4 mm. The spherical projections 3 are similarly formed of synthetic resin such as polyvinyl-alcohol. The width W of the projections 3 is 1 - 1.5 mm in the lengthwise direction of the thread 2. For example, it is 1.2 mm. The distance L between the adjacent projections 3 is 1 - 1.5 mm. For example, it is 1.2 mm.

Next, a method for manufacturing the ligature 1 will be described with reference to FIG. 3 to FIG. 6.

Figure 3:
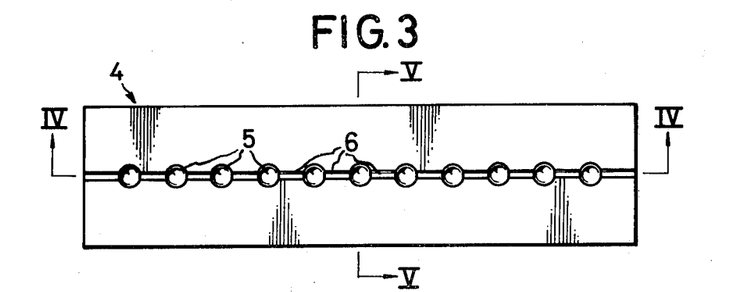
FIG. 3 is a plan view of a mold used for manufacturing the ligature of FIG. 1.
Figure 4:
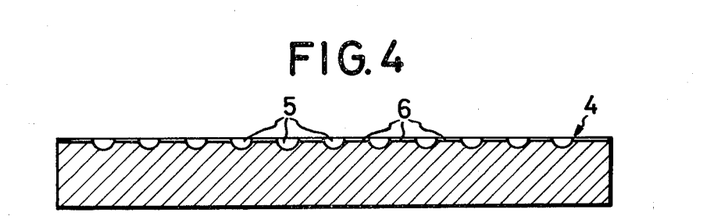
FIG. 4 is a cross sectional view of the mold, taken along the line IV—IV of FIG. 3.
Figure 5:
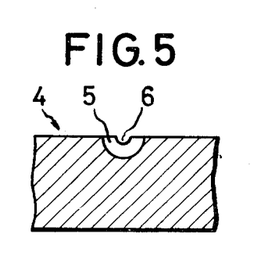
FIG. 5 is a cross sectional view of the mold, taken along the line V—V of FIG. 3.

A mold 4 is used in the method. Hemi-spherical recesses 5 are made at regular intervals of 1.2 mm in a row, in the surface of the mold 4. The diameter of the hemi-spherical recesses 5 is 1.2 mm, corresponding to the shape of the spherical projections 3. Semi-cylindrical grooves 6 are made between the adjacent hemi-spherical recesses 5. The former communicates with the latter. The diameter of the semi-cylindrical grooves 6 is 0.4 mm, corresponding to the shape of the thread 2.

Figure 6:
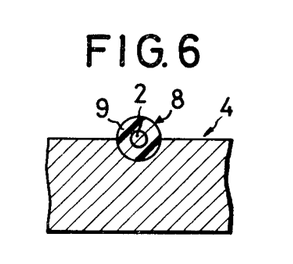
FIG. 6 is a cross sectional view of the mold and the ligature being formed, similar to FIG. 5.

As shown on FIG. 6, the thread 2 formed of synthetic resin such as polyvinyl-alcohol, which has nearly the same diameter as the grooves 6, is fitted into the grooves 6, in predetermined tension. The lower half of the thread 2 is within the grooves 6, while the upper half of the thread 2 projects from the upper surface of the mold 4. Spaces which are semi-annular in cross-section, are formed between the thread 2 and the inner walls of the hemi-spherical recesses 5.

Next, liquid 8 of synthetic resin such as polyvinyl-alcohol is poured into the above described spaces. Portions of the thread 2 facing to the spaces are covered with liquid 8 of synthetic resin, the nearly hemi-spherical swellings 9 are formed on the recesses 5 due to the surface tension phenomenon of the liquid 8.

Next, the liquid 8 of synthetic resin is gradually cooled to solidify. As the result, the synthetic resin 8 firmly adheres to the thread 2 of synthetic resin. The produced ligature 1 is taken out from the mold 4 by pulling upwardly one end of the thread 2. The swelling 9 may be rough. That has the effect that the ligature 1 which is tied to the blood vessel is harder to slip along the blood vessel, as described below.

Figure 7:
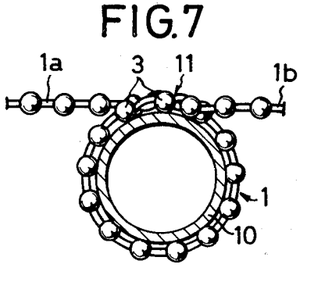
FIG. 7 is a cross sectional view of the blood vessel bound with the ligature.
Figure 8:
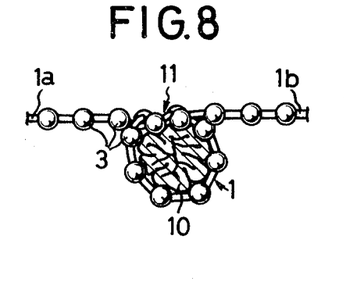
FIG. 8 is a cross sectional view of the blood vessel ligated with the ligature, where the blood vessel is squashed.

Next, a method for ligating the blood vessel with the ligature 1 will be described with reference to FIG. 7 and FIG. 8.

For stopping bleeding, the blood vessel 10 is ligated at a predetermined position with the ligature 1. A desirable ligation can be effected by a single overhand knot of the ligature 1 around the blood vessel 10. First in ligating operation, the ligature 1 is loosely once-knotted around the blood vessel 10, as shown on FIG. 7, and then both ends 1a and 1b of the ligature 1 are pulled strongly in opposite directions. As the result, the blood vessel 10 is ligated with the ligature 1, as shown on FIG. 8. In the ligating state, one of the spherical projections 3 formed at regular intervals in the thread 2 contacts with the thread 2 and another of the spherical projections 3, at a knot position 11. The spherical projections 3 and the thread 2 function as stopper for each other. The frictional force between them effectively prevents the tied ligature from slipping off and loosening, so that a very firm ligation can be effected. Moreover, the frictional force between the spherical projections 3 and the blood vessel 10 prevents the ligature 1 from slipping along the circumference of the blood vessel 10 and slipping in the lengthwise direction of the blood vessel 10.

As above described, the blood vessel 10 can be very firmly and simply ligated by a single knot of the ligature 1 according to this invention in contrast to the conventional method for ligation. When the projections 3 have rough surfaces, the frictional forces among the projections 3 the thread 2 and the blood vessel 10 are larger, and accordingly more firm ligation can be effected.

Figure 9:
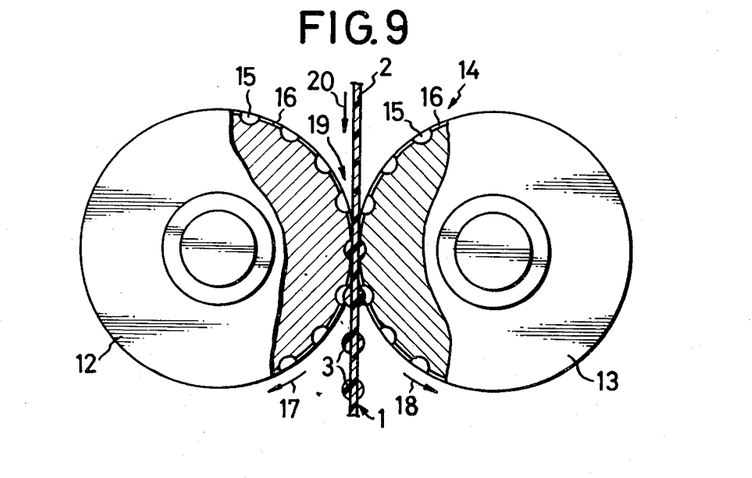
FIG. 9 is a partly cross-sectional view of another mold used for manufacturing the ligature of FIG. 1.

Next, another method for manufacturing the ligature 1 will be described with reference to FIG. 9.

A pair of mold rolls 12 and 13, facing to each other, is arranged in an apparatus used for this method. Hemi-spherical recesses 15 and arched grooves 16 are formed in the circumferences of the mold rolls 12 and 13, corresponding to the shape of the ligature 1. The mold 4 shown on FIG. 3 may be curved to the roll 12 or 13. The rolls 12 and 13 are rotated at a predetermined speed in opposite directions, as shown by the arrows 17 and 18 on FIG. 9. The thread 2 of synthetic resin such as polyvinyl-alcohol is vertically moved through a nipping space 19 between the rolls 12 and 13, in the direction shown by the arrow 20 on FIG. 9, while the liquid of synthetic resin such as polyvinyl-alcohol is poured into the recesses 15 from above the nipping space 19. The thread 2 is nipped at the nipping space 19 between the rolls 12 and 13 to be pressed to the recesses 15 filled with the liquid of synthetic resin. The liquid is cooled to a predetermined solidification temperature at the nipping space 19 or directly under the nipping space 19. Thus, the desired ligature 1, in which the spherical projections 3 are formed at the regular intervals of 1.2 mm in the thread 2 having the diameter 0.4 mm is taken out from the rolls 12 and 13. Of course, the produced ligature 1 has the same effect as the ligature 1 produced by the mold 4 shown on FIG. 3, and the blood vessel 10 can be surely ligated by it. This method is more suitable for the mass production of the ligature 1.

Next, a ligature according to another embodiment of this invention will be described with reference to FIG. 10 to FIG. 16.

Figure 10:
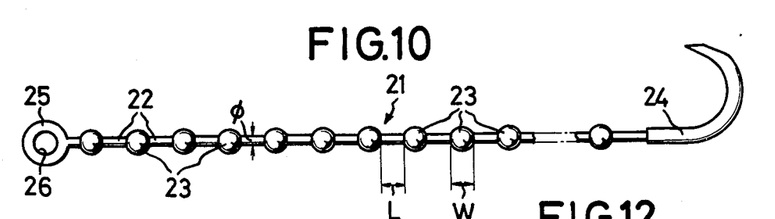
FIG. 10 is a plan view of a ligature according to another embodiment of this invention.

A ligature 21 comprises a thread 22 and spherical projections 23 which are formed integrally with the thread 22 at regular intervals, in the same manner as the ligature 1 according to one embodiment of this invention. However, the ligature 21 according to this embodiment further comprises a hooked needle 24 which is fixed to one end of the thread 22, and threading member 25 having a round hole 26 which is formed integrally with another end of the thread 22.

As in the ligature 1, the thread 22 and the spherical projections 23 are formed of synthetic resin such as polyvinyl-alcohol. The length of the thread 22 is about 80 cm. The diameter $\phi$ of the thread 22 is 0.3 - 0.5 mm. For example, it is 0.4 mm. The width W of the projections 23 is 1 - 1.5 mm. For example, it is 1.2 mm. The distance L between the adjacent projections 23 is 1 - 1.5 mm. For example, it is 1.2 mm. The spherical projections 23 are formed at the regular intervals in the thread 22, using the mold 4 shown on FIG. 3 or the apparatus 14 comprising the pair of rolls 12 and 13 shown on FIG. 9 in the same manner as the ligature 1. The hooked needle 24 is fixed to the one end of the thread 22 by a suitable method. It may be fixed to the one end of the thread 22 by the liquid of synthetic resin in the mold operation of the projections 23. The threading member 25 may be formed integrally with the other end of the thread 22 at the same time when the projections 23 are formed in the thread 22, using the mold 4 shown on FIG. 3. At that case, an annular recess (not shown) is formed in the mold 4, contiguous to the groove 6.

The diameter of the round hole 26 of the threading member 25 is larger than the diameters of the needle 24, the thread 22 and the projections 23. The diameter of the round hole 26 is slightly larger then that of the projections 23. In the ligating operation, the hooked needle 24, the thread 22 and the projections 23 in order can pass through the round hole 26 of the threading member 25 to form a loop round the blood vessel. The spherical projections 23 may be rough.

Next, a method for ligating the blood vessel with the ligature 21 will be described with reference to FIG. 11 to FIG. 16.

In surgical operation, a part of the human body 33 or the tissue is incised. The blood vessel 34 is exposed or embedded in the tissue or positioned inside the human body 33. According to the ligature 21, the blood vessel 34 needs not be drawn out from the inside of the human body 33 or from the tissue with hand or a device. First, the hooked needle 24 of the ligature 21 is stuck into the tissue 33 round the blood vessel 34, and it is rotated round the blood vessel 34 by about 180 degrees. As shown by the dot-dash line on FIG. 11, the hooked needle 24 is taken out from the tissue 33, and so the blood vessel 34 is perfectly caught by the ligature 21.

The hooked needle 24 is further drawn outwardly, and the tip of the hooked needle 24 is inserted through the round hole 26 of the threading member 25. The human body or tissue 33 is not shown in FIG. 12 to FIG. 16. Only the blood vessel 34 is shown.

Figure 13:
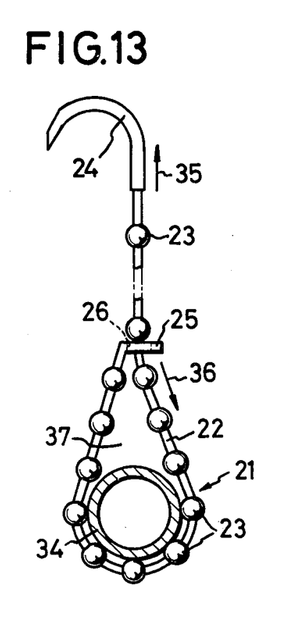
Figure 14:
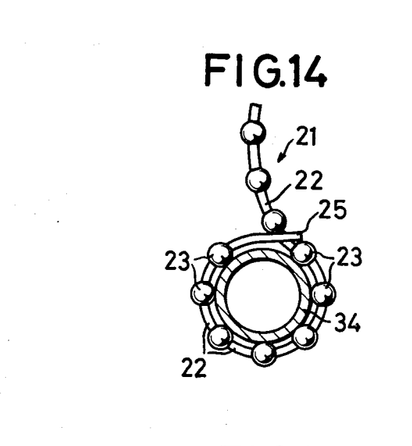

After the hooked needle 24 is inserted through the round hole 26 of the threading member 25, the hooked needle 24 is pulled up in the direction shown by the arrow 35 on FIG. 13, with one hand, while the threading member 25 is pushed down toward the blood vessel 34 in the direction shown by the arrow 36 on FIG. 13, with another hand. The thread 22 and the projections 23 pass through the hole 26 of the threading member 25 to form a loop 37 round the blood vessel 34. The size of the loop 37 is reduced with the pulling-up of the hooked needle 24. At last, the threading member 25 contacts with the blood vessel 34, and the ligature 21 is wound on the blood vessel 34, as shown on FIG. 14.

Figure 15:
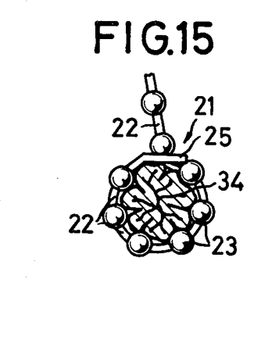

Further, the threading member 25 is pushed down to squash the blood vessel 34, as shown on FIG. 15. In that condition, the ligature 21 cannot be more pulled up. Thus, the ligature 21 is tightly wound on the blood vessel 34 to ligate the latter.

Figure 16:
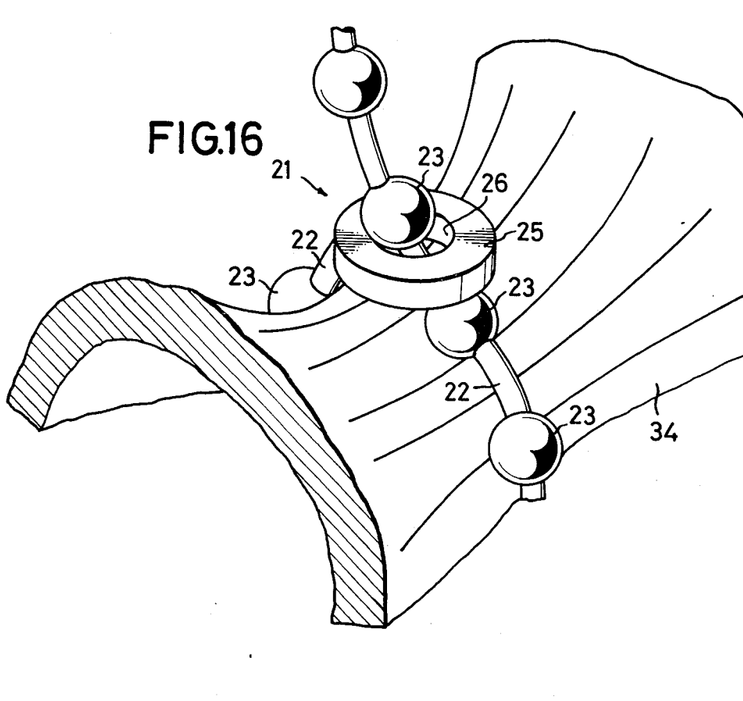
FIG. 16 is an enlarged perspective view of FIG. 15.

In the ligating condition shown on FIG. 15, as apparent from FIG. 16, the one projection 23, which has passed through the hole 26, contacts tightly with the upper edge of the threading member 25, while the adjacent other projection 23, which has not yet passed through the hole 26, contacts tightly with the lower edge of the threading member 25. By the frictional forces among the edges of the threading member 25, the projections 23 and the blood vessel 34, the ligature 21 is surely tied round the blood vessel 34, although the hooked needle 24 and the threading member 25 are separated from the hands of the operator. The shape of the threading member 25, and therefore of the hole 26 is slightly changed with the shape of the blood vessel 34. It is more difficult that the projection 23 passes through the deformed hole 26. Accordingly, the ligature 21 is more surely tied round the blood vessel 34. Moreover, since the frictional forces occur between the projections 23 and the blood vessel 34, the ligature 21 cannot slide along the circumference of the blood vessel 34 and in the lengthwise direction of the blood vessel 34.

The ligature 21 is cut off at the desirable position by a below-described cutting apparatus. The bleeding is surely stopped by the ligature 21 would tightly round the blood vessel 34. The ligating operation is more sure and simple than by the conventional method.

Next, a cutting apparatus for cutting the ligature 21, according to this invention, will be described with reference to FIG. 17 to FIG. 19C.

Figures 17, 18:
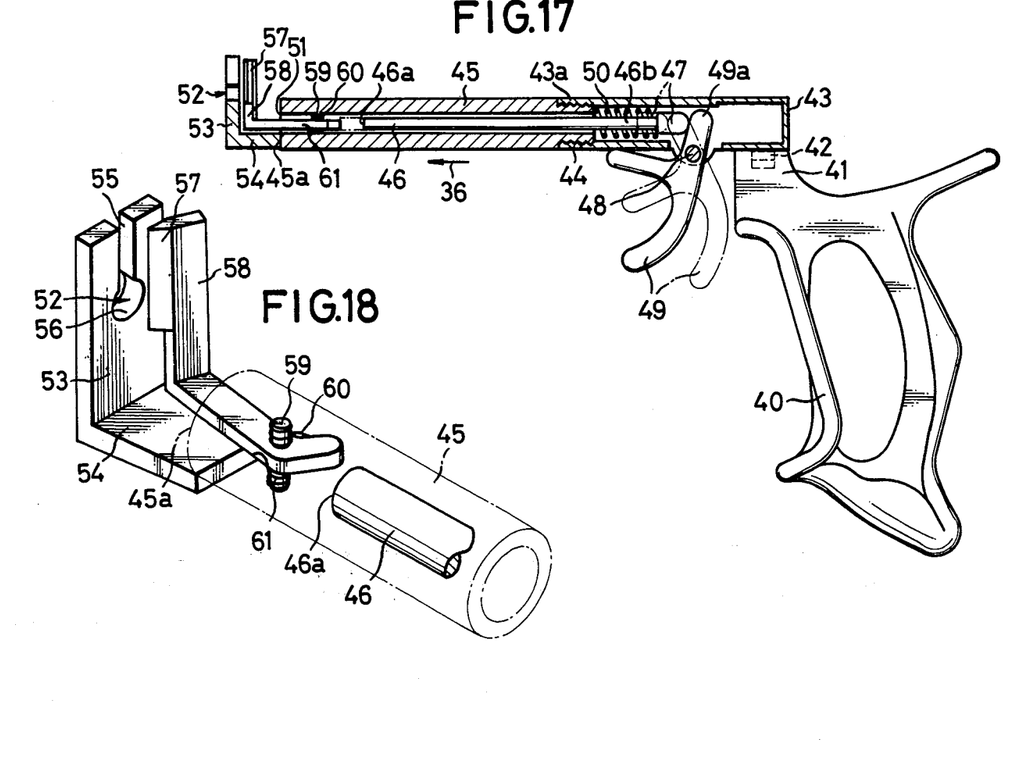
FIG. 17 is a partly cross-sectional view of a cutting apparatus according to this invention, preferably used for the ligature of FIG. 10.
FIG. 18 is an enlarged perspective view of important parts of the cutting apparatus of FIG. 17.
Figure 19A:
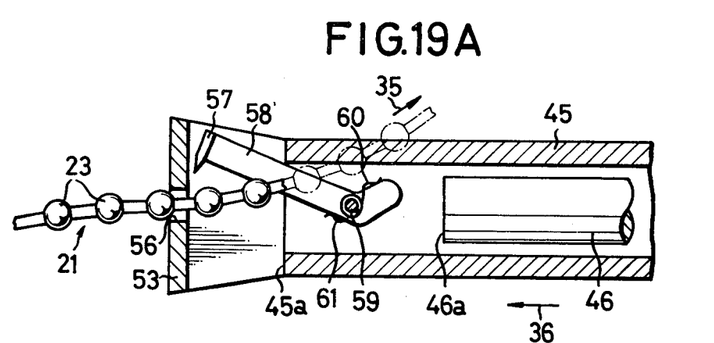
FIG. 19A, FIG. 19B and FIG. 19C are enlarged partly cross-sectional views in plane, of the important parts of the cutting apparatus of FIG. 17, where the sequential steps of the ligating and cutting operation are shown.
Figure 19B:
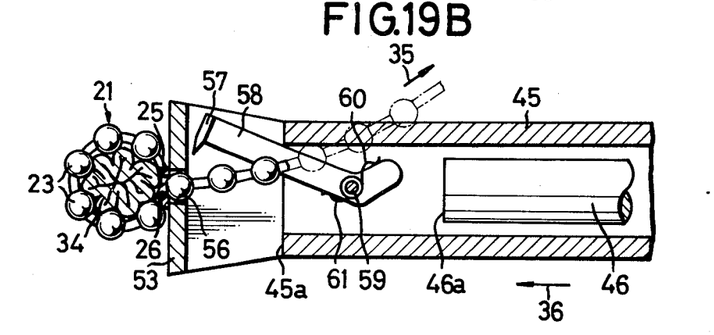
Figure 19C:
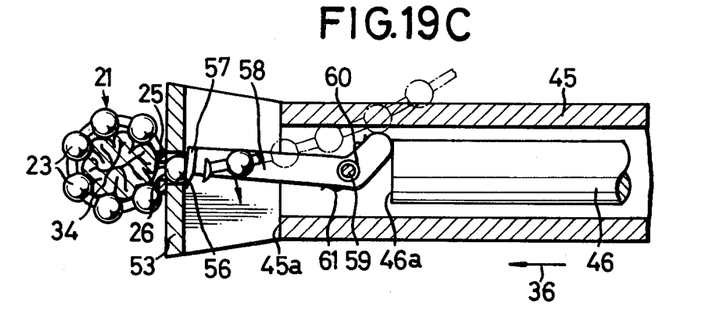

Referring to FIG. 17 and FIG. 18, a cutting apparatus includes a handle 40 formed of metal or synthetic resin, a cylindrical member 43 formed of metal which is fixed to a top portion 41 of the handle 40 by a screw 42, a cylindrical holder 45 which is fixed to the top 43a of the cylindrical member 43 by a screw 44, an actuating rod 46 formed of metal which is slidably inserted into the cylindrical holder 45, and a trigger 49 formed of metal which contacts at its upper end with a contact member 47 fixed to a rear end 46b of the actuating rod 46 and is pivoted to a pin 48 fixed to the cylindrical member 43.

A coil spring 50 is disposed between the rear end of the cylindrical holder 45 and the contact member 47, for restoring the actuating rod 46. A front end 46a of the actuating rod 46 is withdrawn inward from the front opening 51 of the cylindrical holder 45. A ligature holder 53 having the L-shaped cross section is fixed to the front end 45a of the cylindrical holder 45. A cutout 52 like a key hole is formed in the ligature holder 53. The vertical wall of the ligature holder 53 is distant from the rear end 45a of the cylindrical holder 45 by the length of the horizontal wall 54 of the ligature holder 53. The cutout 52 consists of a rectangular hole 55 and a round hole 56 communicating with the rectangular hole 55. The round hole 56 is designed so that the projections 23 can pass through the hole 56, but the threading member 25 cannot pass through the hole 56. A cutter 58 having a knife edge 57 parallel with the vertical wall of the ligature holder 53 is disposed between the ligature holder 53 and the cylindrical holder 45. The cutter 58 is L-shaped, and its one end is bent, as apparent from FIG. 18, which is rotatably supported by a pin 59 fixed to the cylindrical holder 45. Torsion springs 60 and 61 are wound on the upper end and lower end of the pin 59 to urge the cutter 58 in the clockwise direction, so that one side of the cutter 58 contacts with the front end 45a of the cylindrical holder 45, as shown on FIG. 19A and FIG. 19B. When the cutter 58 is rotated in the counter-clockwise direction, the knife edge 57 passes closely by the hole 56 of the ligature holder 53.

Next, operations of the above-described cutting apparatus will be described.

Figure 11:
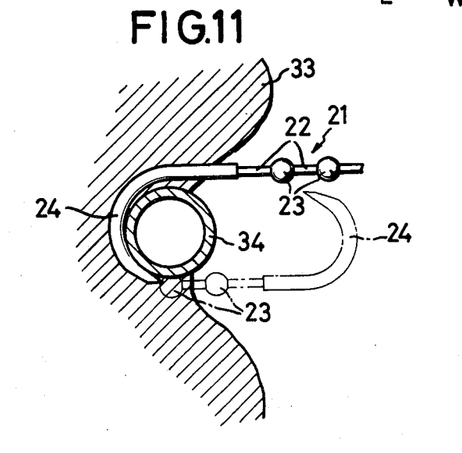
FIG. 11 is a cross sectional view showing the situation that the hooked needle of the ligature is thrust arround the blood vessel inside the human body.
Figure 12:
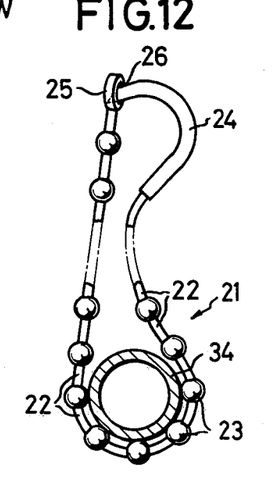
FIG. 12 to FIG. 15 are partly cross-sectional views of the sequential steps of the ligating operation, following the step of FIG. 11, using the ligature of FIG. 10.

As shown on FIG. 11, FIG. 12 and FIG. 13, the blood vessel 34 is caught by the ligature 21. The thread 22 of the ligature 21 between the hooked needle 24 and the loop 37 (see FIG. 13) is put into the round hole 56 of the ligature holder 53 through the rectangular hole 55 thereof, as shown on FIG. 19A. In that condition, the hooked needle 24 is held by one hand of an operator, while the handle 40 of the apparatus is held by another hand of the operator. The hooked needle 24 is pulled in the direction shown by the arrow 35, while the apparatus is moved toward the blood vessel 34 in the direction shown by the arrow 36 on FIG. 19A. The ligature 21 successively passes through the round hole 56 of the ligature holder 53. As the result, the threading member 25 of the ligature 21 comes to contact with the ligature holder 53, as shown on FIG. 19B. Since the size of the threading member 25 is larger than that of the hole 56, the threading member 25 cannot pass through the hole 56. Accordingly, the threading member 25 is stopped by the ligature holder 53, and only the projections 23 and the thread 22 can pass through the hole 56. When the blood vessel 34 is squashed, the threading member 25 is pressed between the blood vessel 34 and the ligature holder 53, and moreover the ligature holder 53 is positioned inside the human body.

Next, the trigger 49 shown on FIG. 17 is drawn backward to the position shown by the dot-dash line on FIG. 17. The contact member 47 is pushed by the upper end 49a of the trigger 49, so that the actuating rod 46 is moved forward in the direction shown by the arrow 36 within the cylindrical holder 45 against the coil spring 50.

With the movement of the actuating rod 46, the front end 46a of the actuating rod 46 pushes the bent end of the cutter 58 to rotate the cutter 58 in the counterclockwise direction against the torsion springs 60 and 61. With the rotation of the cutter 58, the ligature 21 is cut off by the knife edge 57 of the cutter 58, as shown on FIG. 19C. The more sharp the edge of the hole 56, the easier the cutting of the ligature 21.

Thus, the ligature 21 can be cut off at the desired position in the condition that the blood vessel 34 is surely ligated by the ligature 21 without drawing out from the inside of the human body 33. The tie of the ligature 21, the stop of bleeding and the cutting of the ligature 21 can be successively effected by the apparatus according to this invention. Accordingly, the ligating operation can be remarkably simplified in comparison with the conventional method.

After cutting the ligature 21, the trigger 40 is separated from the hand of the operator. The trigger 40 and the actuating rod 45 is restored to their original positions by the coil spring 50. And the cutter 58 is rotated back to its original position in the clockwise direction by the torsion springs 60 and 61.

Of course, the apparatus of FIG 17 can be used for cutting the ligature 1 of FIG. 1 also.

Figure 20:
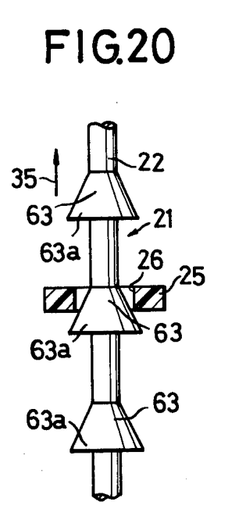
FIG. 20 to FIG. 25 are partly cross-sectional views or elevational views of parts of ligatures according to still further embodiments of this invention.
Figure 21:
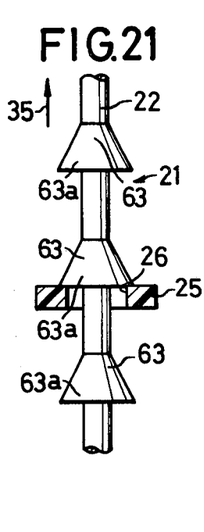

FIG. 20 and FIG. 21 show a further embodiment of this invention. This embodiment is different from the embodiment of FIG. 10 only in the shape of the projections. The parts in this embodiment which correspond to the parts in the embodiment of FIG. 10, are denoted by the same reference numerals, which will not be described in detail.

In this embodiment, cone-shaped projections 63 are formed at regular intervals in the thread 22. Surfaces 63a of the cone-shaped projections 63 taper in the pulling direction shown by the arrow 35 on FIG. 20, of the ligature 21, and they are elastic. Accordingly, the cone-shaped projections 63 yield to the hole 26 of the threading member 25 and can smoothly pass through the hole 26 of the threading member 25 although the bottom diameter of the cone-shaped projections 63 is slightly larger than the diameter of the hole 26 of the threading member 25, as shown on FIG. 20 and FIG. 21. After passing through the hole 26, the cone-shaped projection 63 is restored to its original shape, as shown on FIG. 21. Accordingly, it cannot pass through the hole 26 in the direction opposite to the direction shown by the arrow 35 on FIG. 21. Since the ligature 21 is prevented from moving in the direction opposite to the direction shown by the arrow 35, the ligature 21 ligating the blood vessel is prevented from loosening.

Figure 22:
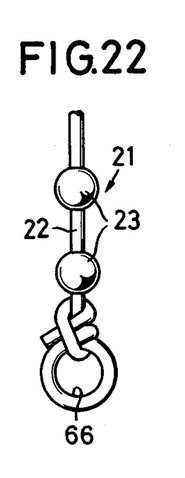

FIG. 22 shows a ligature according to a still further embodiment of this invention. This embodiment is different from the embodiment of FIG. 10 in the construction of the threading member. In this embodiment, the threading member is constructed in such a manner that the end portion of the thread 22 is double-knotted to form a round hole 66. The method for ligating the blood vessel with the ligature 21 of FIG. 22 is the same as with the ligature 21 of FIG. 10.

Figure 23:
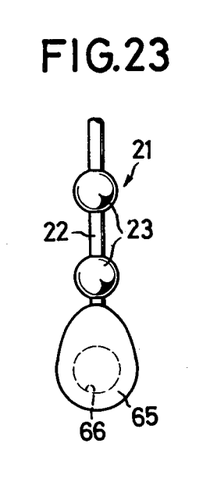
Figure 24:
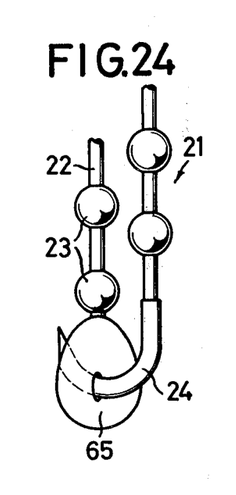

FIG. 23 and FIG. 24 show a ligature according to a still further embodiment of this invention. Also this embodiment is different from the embodiment of FIG. 10 in the construction of the threading member. In this embodiment, the threading member 25 of the ligature 21 of FIG. 10 is dipped into the liquid of polyvinylalcohol to form a disk-like film 65 covering the hole 66. In the ligating operation, the blood vessel is caught by the ligature 21, as shown on FIG. 11, and then the film 65 is pierced nearly at the center with the tip of the hooked needle 24, as shown on FIG. 24. Since the film 65 of polyvinylalcohol is thin, the hooked needle 24 and the projections 23 can easily pass through the threading member 65 comprising the film. Hereafter, the blood vessel can be ligated with the ligature 21 in the same manner as in the method described above for the ligature 21 of FIG. 10. By the disk-like film 65, the shape of the hole 66 is almost unchanged both when the ligature 21 is not in use, and when it is in use.

Figure 25:
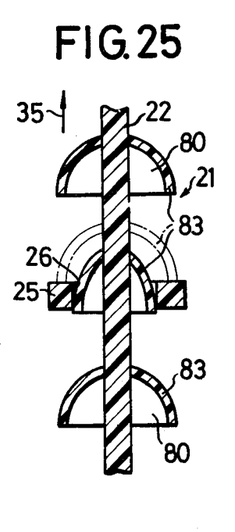

FIG. 25 shows a ligature according to a still further embodiment of this invention. This embodiment is different from the embodiment of FIG. 10 only in the shape of the projections. In this embodiment, bowl-like projections 83 having a hemi-spherical space 80 are formed at the regular intervals in the thread 22. Since the projections 83 are elastic, they yield to the shape of the hole 26 of the threading member 25, and can pass easily through the hole 26, as shown on FIG. 25. After passing through the hole 26, the projections 83 are restored to their original shape, as shown by the dot-dash line on FIG. 25. Accordingly, the ligature 21 cannot be pulled in the direction opposite to the direction shown by the arrow 35 on FIG. 25.

Although illustrative embodiments of this invention have been described in detail herein with reference to the accompanying drawings, it is to be understood that the invention is not limited to those precise embodiments, and that various changes and modifications may be effected therein by one skilled in the art without departing from the spirit and scope of the novel concepts of this invention, as defined in the appended claims.

For example, the shape of the projections may be unsymmetrical with respect to the lengthwise direction of the thread. The projections may be formed at irregular intervals in the thread. The thread and the projections may be formed at the same time in such a manner that the liquid of synthetic resin is poured both into the recesses 5 and into the grooves 6, in the mold 4 of FIG. 3.

The surgical thread according to this invention can be used not only as the ligature, but also as the stitching thread.

Moreover, in the cutting apparatus, the cutter may be arranged in the ligature holder 53, not in the cylindrical holder 45.

What is claimed is:

1. A surgical thread comprising a thread-like body and a plurality of integrally molded projections formed at intervals in said thread-like body, a needle member attached to one end of said thread-like body, and a threading member formed on another end of said thread-like body, said threading member comprising a ring-shaped body, a thin film formed around said threading member, said film extending over said ring-shaped body, said needle member being adapted to pierce said film to form an opening through said ring-shaped body through which said needle member, said thread-like body and said projections can pass to form a loop around an object, one of said projections being secured by said ring-shaped body when said object is held by said loop.

2. A surgical thread according to claim 1 wherein said thread-like body has a diameter between about 0.3 and 0.5 mm., said projections having a diameter between about 1 and 1.5 mm., and the distance between adjacent projections being between about 1 and 1.5 mm.

3. A surgical thead according to claim 1, in which said thread-like body and said projections are formed of synthetic resin.

4. A surgical thread according to claim 3, in which said synthetic resin is polyvinyl-alcohol.

5. A surgical thread according to claim 1, in which said projections are spherical.

6. A surgical thread according to claim 1, in which said projections are cone-shaped, the surfaces of said projections tapering to the direction in which said surgical thread is pulled during the ligating operation.

7. A surgical thread according to claim 1, in which said projections are bowl-like shaped, the surfaces of said projections tapering to the direction in which said surgical thread is pulled during the ligating operation.

8. A surgical thread according to claim 1, in which said needle member is hooked.

9. A surgical thread according to claim 1, in which said threading member is formed integrally with said thread-like body.

* * * * *